United States Patent [19]
Kaswan et al.

[11] Patent Number: 5,639,743
[45] Date of Patent: Jun. 17, 1997

[54] COMPOSITIONS AND METHODS FOR TREATING EXOCRINE GLAND ATROPHY

[75] Inventors: Renee Kaswan, Athens, Ga.; Austin K. Mircheff, LaCrescenta; Dwight W. Warren, Granada Hills, both of Calif.

[73] Assignees: University of Georgia Research Foundation, Athens, Ga.; University of Southern California, Los Angeles, Calif.

[21] Appl. No.: 268,971

[22] Filed: Jun. 30, 1994

Related U.S. Application Data

[63] Continuation of Ser. No. 975,869, Nov. 13, 1992, abandoned.

[51] Int. Cl.$^6$ .......... A61K 31/56; A61K 31/495; A61K 31/50; A61K 31/40
[52] U.S. Cl. .......... 514/171; 514/177; 514/250; 514/254; 514/410
[58] Field of Search .......... 514/250, 254, 514/177, 171, 410

[56] References Cited

U.S. PATENT DOCUMENTS

| | | | |
|---|---|---|---|
| 4,565,821 | 1/1986 | Chiou | 514/327 |
| 4,701,450 | 10/1987 | Kelder et al. | 514/177 |
| 4,772,616 | 9/1988 | Chiou | 514/322 |
| 4,839,342 | 6/1989 | Kaswan | 514/11 |
| 5,041,434 | 8/1991 | Lubkin | 514/182 |
| 5,041,450 | 8/1991 | Chiou et al. | 514/288 |

OTHER PUBLICATIONS

Mircheff, Austin K., "Lacrimal Fluid and Electrolyte Secretion: A Review," 8(6) *Curr. Eye Res.* 607–617 (1989).
Dartt, Darlene A., "Signal Transduction and Control of Lacrimal Gland Protein Secretion: A Review," 8(6) *Curr. Eye Res.* 619–636 (1989).
Ariga, Hiroko, et al., "Androgen Control of Autoimmune Expression in Lacrimal Glands of MRL/Mp–Ipr/Ipr Mice," 53 *Clin. Immunol. Immunopathol.* 499–508 (1989).
Sullivan, David A., "Influence of the Hypothalamic–Pituitary Axis on the Androgen Regulation of the Ocular Secretory Immune System," 30 *J. Steroid Biochem.* 429–433 (1988).
Sullivan, David A., & M.R. Allansmith, "Hormonal Modulation of Tear Volume in the Rat," 42 *Exp. Eye Res.* 131–139 (1986).
Cornell–Bell, Ann H., et al., "Gender–Related Differences in the Morphology of the Lacrimal Gland," 26(8) *Invest. Ophthalmol. Vis. Sci.* 1170–1175 (1985).
Yiu, Samuel, C., et al., "Stimulation–Associated Redistribution of Na,K–ATPase in Rat Lacrimal Gland," 102 *J. Membrane Biol.* 185–194 (1988).
Bradley, Michael, E., et al., "Subcellular Distribution of Muscarinic Acetylcholine Receptors in Rat Exorbital Lacrimal Gland," 31 *Invest. Ophthalmol. Vis. Sci.* 977–986 (1990).
Murer, Heini, et al., "The Surface Membrane of the Small Intestinal Epithelial Cell: I. Localization of Adenyl Cyclase," 433 *Biochem. Biophys. Acta.*, 509–519 (1976).
Warren, Dwight W., et al., "Prolactin Binding and Effects on Peroxidase Release in Rat Exorbital Lacrimal Gland," 31 (4 Abst. Issue) *Invest. Ophthalmol. Visual Sci.* 540 (1990).
Kelleher, Robin S., et al., "Secretory Component Synthesis by Lacrimal Gland Acinar Cells Impact of Endocrine and Culture Environment," 31 (4 Abstr. Issue) *Invest. Ophthalmol. Visual Sci.* 63 (1990).
Zierhut, M., et al., "Bromocriptin: ein neues Therapiekonzept in der Behandlung der chronisch rezidivierenden Uveitis?" (Bromocriptine: A New Therapeutic Concept in the Treatment of Chronic Recurrent Uveitis?), 195 *Klin. Mbl. Augenheilk.* 221 (1989). (A written English translation is not within Applicants' possession. However, the abstract in English is printed on p. 1 of the reference).
Plever, U., et al., "Prolactin in Human Aqueous Humor," 11 (5) *Neuro Endocrinology Letters* 278 (1989).
Ebling, F.J., et al., "The Synergistic Action of α–Melanocyte–Stimulating Hormone and Testosterone on the Sebaceous, Prostate, Preputial, Harderian and Lachrymal Glands, and Seminal Vesicles and Brown Adipose Tissue in the Hypophysectomized–Castrated Rat," 66 *J. Endocr.* 407–412 (1975).
Mircheff, Austin K., et al., "Prolactin Localization, Binding, and Effects on Peroxidase Release in Rat Exorbital Lacrimal Gland," 33(3) *Invest. Ophthalmol. Visual Sci.* 641–650 (1992).
Azzarola, AnaMaria, et al., "Dihydrotestosterone and Prolactin Reverse Lacrimal Gland Regression After Hypophysectomy of Female Rats," 31 (4 Abst. Issue) *Invest. Ophthalmol. Visual Sci.* 1290 (Mar. 15, 1992).

*Primary Examiner*—Theodore J. Criares

[57] ABSTRACT

Methods and compositions for the prevention or reversal of exocrine gland atrophy, especially lacrimal gland atrophy, by maintaining normal physiological levels of prolactin are described. In the preferred embodiment, exogenous prolactin or a substance that modulates endogenous prolactin secretion is administered to a mammal in combination with an androgen, such as testosterone. The combination acts synergistically to maintain or restore normal prolactin concentrations, resulting in the maintenance or restoration of gland mass and function. Administration of prolactin and androgen in combination with estrogen is particularly useful in the treatment of lacrimal gland dysfunction in postmenopausal women or women who have undergone ovariohysterectomies.

19 Claims, 5 Drawing Sheets

COMPOSITIONS AND METHODS FOR TREATING EXOCRINE GLAND ATROPHY

This is a continuation of application Ser. No. 07/975,869 filed on Nov. 13, 1992, now abandoned.

The United States government has rights in this invention by virtue of National Institutes of Health grant number EY RO1-05801 and Biomedical Research Support Grant number SO7-RR05356.

This relates to the field of ophthalmology and more specifically relates to a method and compositions for preventing or restoring exocrine gland atrophy.

BACKGROUND OF THE INVENTION

Keratoconjunctivitis sicca (KCS), or "dry eye" is an eye disorder caused by an absolute or partial deficiency in lacrimal gland fluid production. This disorder is one of the most common complaints in ophthalmology. Normally, the exposed portion of the eye is covered by a thin layer of fluid, or tear film, supplied by the lacrimal gland. This fluid is important for the well-being of the corneal and conjunctival epithelium and provides the cornea with an optically high quality surface. Lacrimal fluid acts as a lubricant between the ocular surface and the eyelids and contains proteins such as immunoglobulin A, lysozyme and beta lysin, which are known to have bacteriostatic properties. One component of the tear film, mucin, helps the tears to flow evenly over the eye and is produced by specific cells that are stimulated by specialized nerves. Insufficient production of lacrimal gland fluid is one of the most frequent causes of "dry eye".

Physiology of Lacrimal Secretion

The lacrimal gland is a typical tubulo-acinar gland located in the superior and inferior aspects of the orbit, which secretes an electrolyte, protein, nutrient, and immunoglobulin-containing fluid in two stages, first in the acini and then in the ducts. Little is known about ductal function. The acini account for 80% of the mass of the gland. Some of the proteins in lacrimal gland fluid are synthesized within the acinar cells, then packaged, and secreted by the classical exocytotic mechanism. The immunoglobulins are secreted by a transcytotic mechanism in which a crucial role is played by the polymeric immunoglobulin receptor (referred to as PIgR or secretory component, SC). The secretion of electrolytes and therefore most of the fluid is driven by the sodium pump enzyme Na, K-ATPase (Mircheff, Current Eye Research 8, 607–617, 1989).

The secretory functions of the acinar cell are acutely regulated, primarily by autonomic secretomotor innervation. The innervation is known to be mediated by a variety of receptors, including muscarinic cholinergic, VIP-ergic, and α- and beta-adrenergic receptors, as reviewed by Dartt, D. A., Current Eye Research 8:619–636. Lacrimal acinar cells also contain signal-transducing receptors for a variety of peptide hormones and other mediators, including α-melanocyte stimulating hormone (α-MSH), adrenocorticotrophic hormone (ACTH), prolactin and enkephalins. In contrast to the cholinergic, VIP-ergic, and adrenergic receptors, the enkephalin receptor is coupled to inhibitory G proteins that block the responses to cholinergic receptors and VIP.

Several differences between the lacrimal glands of male and female animals have been documented. Ariga et al., Clin. Immunol. Immunopathol. 53:499–508, 1989; Sullivan et al., J. Steroid Biochem. 30:429–433, 1988; Sullivan et al., Exp. Eye Res. 42:131–139, 1986; Cornell-Bell et al., Invest. Ophthalmol. Vis. Sci. 26:1170–1175, 1985. The acinar cells are significantly larger, PIgR synthesis is greater, and more IgA is secreted in male rats. However, there have been no direct comparisons between lacrimal gland fluid secretion rates in male and female animals. Castration of male rats leads to increases in precorneal tear volume and to decreases in PIgR synthesis and IgA secretion. Treatment of castrated rats with testosterone reverses these changes. However, if rats are both castrated and hypophysectomized (pituitary surgically removed), testosterone replacement does not reverse the changes induced by castration.

Symptoms and Treatment of KCS

In relatively mild cases of KCS, the main symptom is a foreign body sensation or a mild "scratchiness". This can progress to a constant intense burning or irritative sensation that can become debilitating. More severe forms progress to the development of filamentary keratitis, a painful condition characterized by the appearance of numerous strands of filaments attached to the corneal surface. Recent evidence suggests that these filaments represent breaks in the continuity of corneal epithelial cells. The shear created by lid motion pulls these filaments, causing pain. Secondary infection is a frequent complication of KCS. This breakdown in the normal defense mechanism of the eye is most likely attributable to a decrease in the concentration of antibacterial lysozyme in the lacrimal fluid or a decrease in the available quantity of lacrimal fluid.

Although KCS can develop in the absence of any other overt systemic abnormality, there is a frequent association of KCS with systemic disease. KCS can occur as part of a larger systemic involvement known as Sjögren's syndrome, an autoimmune disorder characterized by dry eyes, dry mouth, and arthritis. Sjögren's syndrome is recognized as a dysfunction of the lacrimal gland wherein the gland is infiltrated by mononuclear cells that ultimately leads to destruction, or atrophy, of the glandular structure. These patients are also characterized by decreased secretion of all mucous membranes, causing gastrointestinal, urological, and vaginal distress.

Most dry eye patients, and the vast majority of Sjögren's syndrome patients, are postmenopausal women. Additionally, oral contraceptive use, pregnancy, and lactation are frequently associated with contact lens intolerance believed to result from lacrimal insufficiency.

Conventional treatment of KCS and other dry eye disorders alleviates the symptoms of the dry eye state but does not cure the underlying disorders or causes of the disease. Currently, aqueous-deficient, dry eye patients are treated by supplementation of lacrimal fluid with artificial tear substitutes. Relief is limited by the retention time of the administered artificial tear solution in the eye, which typically dissipates within about thirty to forty-five minutes. Therefore, the effect of such products, while initially soothing, does not persist for a sufficient amount of time to cause measurable relief and the patient is inconvenienced by the need for repeated administration of the artificial tear solution in the eye.

U.S. Pat. No. 4,839,342 to Kaswan reported that another method to increase lacrimal gland production was by topical treatment with cyclosporin, an immunosuppressant. The long term effectiveness of this treatment has not yet been determined in humans. Moreover, it is limited to treatment of dry eye, even in those patients suffering from decreased secretion in multiple glands.

It can thus be readily appreciated that a method or composition that prevents or restores lacrimal gland mass atrophy, resulting in an increase in lacrimal gland fluid production, as well as of other secretory exocrine glands, is needed.

It is therefore an object of the present invention to provide a treatment for keratoconjunctivitis sicca.

It is a further object of the present invention to provide a treatment for lacrimal insufficiency in women caused by menopause or ovariohysterectomy.

It is a further object of the present invention to provide compositions and methods for maintaining or restoring normal prolactin levels.

It is another object of the present invention to provide compositions and methods for maintaining or restoring normal exocrine gland mass and function.

SUMMARY OF THE INVENTION

Compositions and methods for the prevention or reversal of atrophy of the lacrimal and other secretory exocrine glands are described. Exogenous prolactin, or a substance that modulates endogenous prolactin secretion, or an androgen, such as testosterone, is administered to a mammal alone or in combination. The combination acts synergistically to maintain or restore normal prolactin concentrations, resulting in the maintenance or restoration of exocrine gland mass and function. The compositions and methods are particularly useful in combination with estrogen supplementation for the treatment of autoimmune disorders such as lacrimal gland dysfunction in post-menopausal women or women who have undergone ovariohysterectomies.

BRIEF DESCRIPTION OF THE DRAWINGS

FIG. 2a shows the specific activity of Na,K-ATPase (nmole/mg protein/hr). FIG. 2b shows total Na,K-ATPase activity (nmole/hr). FIG. 2c shows specific activity of cholinergic receptor binding (fmole bound/mg protein). FIG. 2d shows total cholinergic receptor binding (fmole bound). FIG. 2e shows specific activity of beta-adrenergic receptor binding (fmole bound/mg protein). FIG. 2f shows total beta-adrenergic receptor binding (fmole bound).

FIG. 3a is a measurement of total protein (mg). FIG. 3b is a measurement of lacrimal gland weight (mg). FIG. 3c shows the specific activity of Na,K-ATPase (nmole/ mg protein/hr). FIG. 3d shows total Na,K-ATPase activity (nmole/hr). FIG. 3e shows specific activity of cholinergic receptor binding (fmole bound/mg protein). FIG. 3f shows total cholinergic receptor binding (fmole bound). FIG. 3g shows specific activity of beta-adrenergic receptor binding (fmole bound/mg protein). FIG. 3h shows total beta-adrenergic receptor binding (fmole bound).

FIG. 4a is a measurement of total protein (mg). FIG. 4b shows the specific activity of Na,K-ATPase (nmole/mg protein/hr). FIG. 4c shows specific activity of cholinergic receptor binding (fmole bound/mg protein). FIG. 4d shows specific activity of beta-adrenergic receptor binding (fmole bound/mg protein).

DETAILED DESCRIPTION OF THE INVENTION

Figure 1:
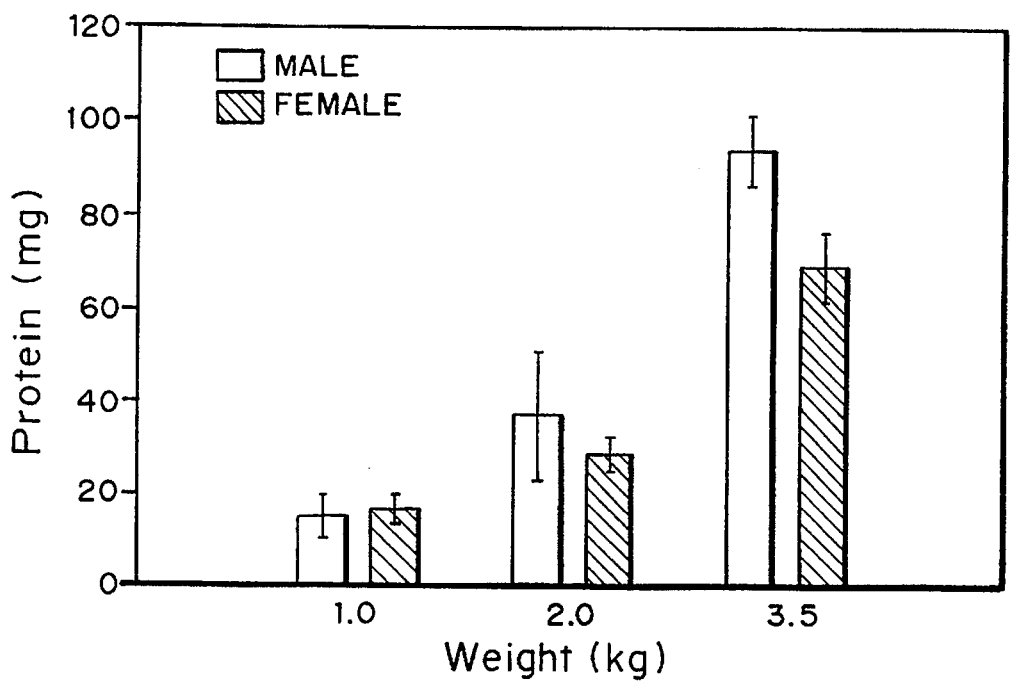
FIG. 1 is a bar graph showing the protein content of male and female rabbit lacrimal glands as a function of weight of the rabbit (kg). The open bars represent the protein content (mg) of male rabbit lacrimal glands. The hatched bars represent the protein content of female rabbit lacrimal glands.
Figure 2A:
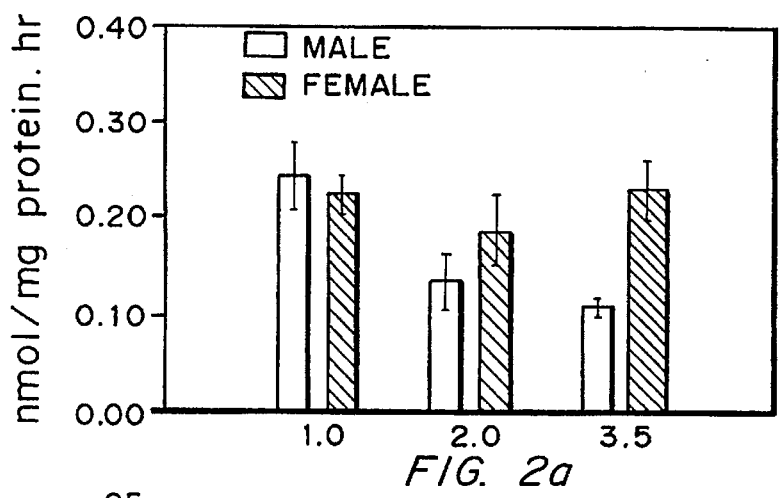
FIGS. 2a–f are bar graphs showing the results of several measures of lacrimal gland function in male and female rabbits as a function of lacrimal gland weight (kg of rabbit weight). The open bars represent the protein content of male rabbit lacrimal glands. The hatched bars represent the. protein content of female rabbit lacrimal glands.
Figure 2B:
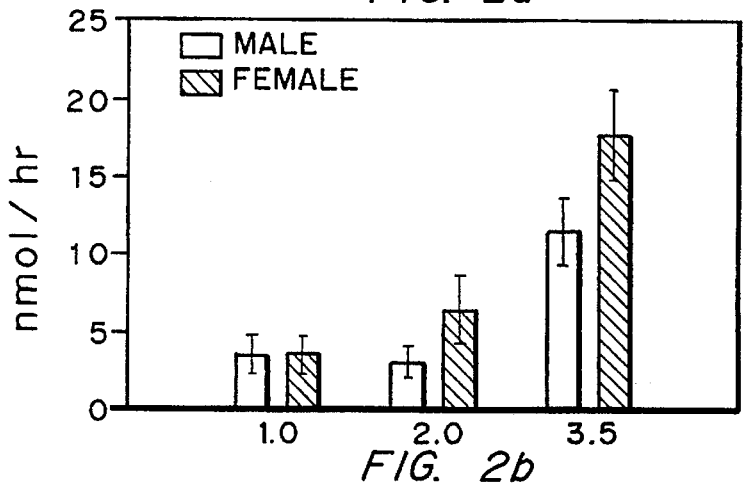
Figure 2C:
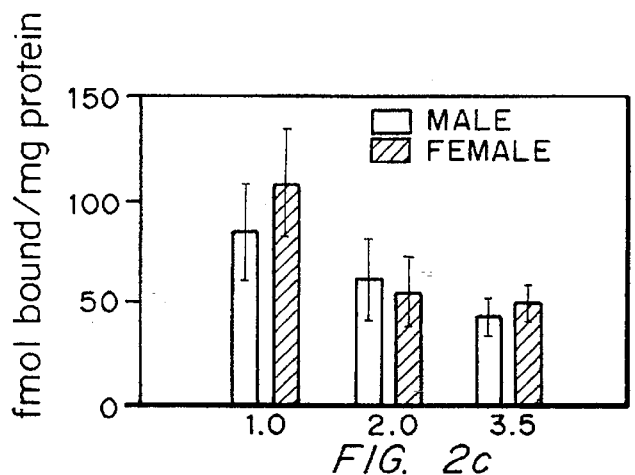
Figure 2D:
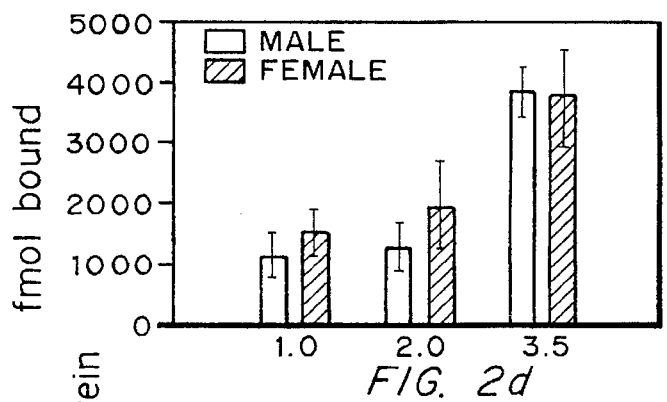
Figure 2E:
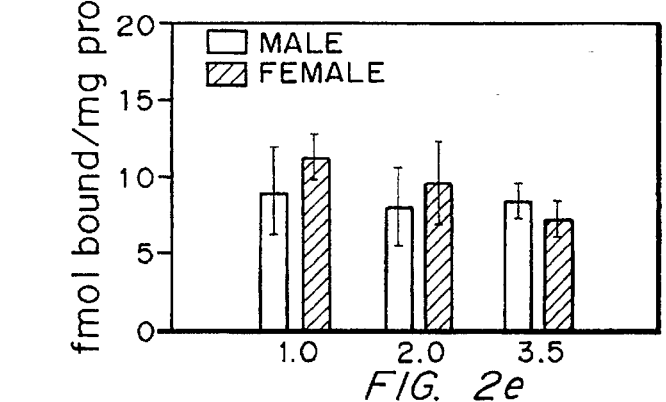
Figure 2F:
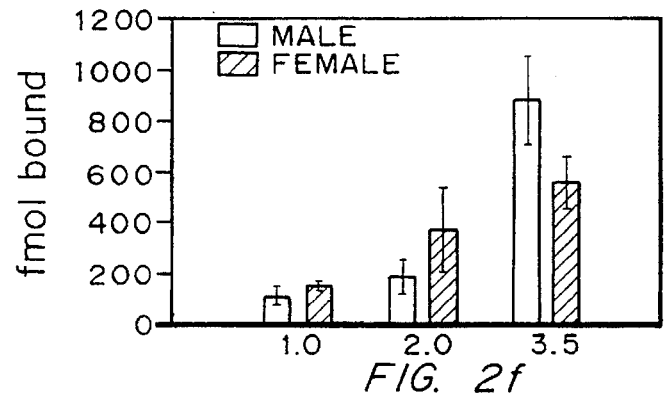

Compositions and methods are provided herein for use in the prevention of exocrine gland atrophy and restoration of exocrine gland mass, resulting in improved exocrine gland fluid production and alleviation of the symptoms and causes of eye disorders such as keratoconjunctivitis sicca (KCS). Due to ease of measurement of effect, lacrimal gland function is used to demonstrate the effectiveness of this therapy.

In the preferred embodiment, exogenous prolactin, or a substance that modulates endogenous prolactin secretion, is administered to a mammal in combination with an androgen, such as testosterone in a pharmaceutically acceptable carrier. In alternative embodiments, the prolactin or the androgen are administered alone, in an amount effective to increase secretion levels. The combined therapy maintains or restores prolactin and androgen concentrations to optimal levels, resulting in the maintenance or restoration of exocrine gland mass and function. "Optimal levels", as used herein, means that the therapy is effective at increasing secretion in an amount to between the pre-treatment levels and normal levels, as measured using standard clinical parameters. "Normal" levels may not be achieved in all cases, although sufficient function is obtained to provide relief from the disorder. The combined prolactin and androgen therapy can be administered separately, or as a composition containing both the prolactin, or prolactin modulating substance, and the androgen in a single administration.

As described above, there are many disorders characterized by insufficient secretion by the exocrine glands. The compositions and methods are particularly useful in combination with estrogen for the treatment of exocrine gland dysfunction in post-menopausal women or women who have undergone ovariohysterectomies. The compositions and methods are also useful in the treatment of dry eye and other disorders associated with autoimmune disorders such as Sjogren's syndrome.

Exocrine gland atrophy causes exocrine gland disfunction, resulting in insufficient exocrine gland fluid production. Abnormally high or low levels of prolactin in the body appear to affect the exocrine gland adversely. Restoration of prolactin to normal physiological levels, or levels approximating normal, is necessary to either prevent or inhibit exocrine gland atrophy or to restore or enhance exocrine gland mass and function. However, administration of prolactin, or a prolactin agonist or antagonist, alone is not sufficient to restore or maintain optimal lacrimal gland mass and function. An androgen, such as testosterone or testosterone derivatives, must be administered in combination with the prolactin therapy to prevent or restore exocrine gland mass atrophy. Preferably, in female patients that have abnormally low physiological estrogen levels, such as patients who are post-menopausal or have had ovariohysterectomies, the combined prolactin and androgen therapy should be further combined with the administration of estrogen in order to achieve optimal physiological prolactin levels. By inhibiting exocrine gland atrophy or increasing the mass of an exocrine gland that has already atrophied to a normal size, exocrine gland function is preserved or restored and adequate amounts of exocrine gland fluid is produced.

The prolactin or prolactin secretion inducing compounds, androgens, and estrogens described below are commercially available in appropriate pharmaceutical carriers for administration to a patient. The composition and method of administration for these compounds are established and known to those in the medical or pharmaceutical field.

Prolactin

Prolactin is a protein hormone secreted by acidophil cells in the adenohypophysis portion of the anterior pituitary gland (pars distalis). Human prolactin is composed of 198 amino acids and has a molecular weight of approximately 23,000 daltons. The structure of prolactin is further characterized by the presence of three disulphide bridges between the cysteine amino acids in the peptide sequence. Prolactin is associated with mammary gland stimulation, causing milk production in female mammals. Prolactin is found in both males and females of all vertebrates. Prolactin is found in normal human blood at a mean concentration of 14.0±5 µg/L in females and 12±3.2 µg/L in males.

Modulation of Endogenous Prolactin Secretion

The level of endogenous prolactin in the body can be increased or decreased so that it is maintained or restored to normal physiological blood concentrations in various ways. The preferred method of increasing suboptimal physiologic prolactin levels is by direct administration of prolactin from another source, such as purified prolactin from animal or human sources or recombinant prolactin (i.e., prolactin produced by recombinant DNA techniques). This exogenous prolactin is preferably administered intramuscularly at a dose of between approximately 0.5 and 5.0 mg, but it is to be understood by one of ordinary skill in the art that other methods of administration may be equally effective.

The preferred method of decreasing elevated physiologic prolactin levels is by administration of a prolactin antagonist such as bromocriptine mesylate. Bromocriptine is an ergot derivative that appears to be a partial agonist at presynaptic dopamine type-2 receptors. Bromocriptine is widely used in the treatment of endocrinologic disorders, especially hyperprolactinemia. It is commercially available from Sandoz Pharmaceutical, East Hannover, N.J., as the prescription drug Parlodel™. Preferably, a dose of 2.5–5 mg is administered orally two or three times daily.

An alternative method of increasing prolactin levels is to administer a substance that will stimulate the secretion of endogenous pituitary prolactin. Cysteamine (2-aminoethanethiol) is a sulfhydryl reducing agent used clinically to elevate hepatic stores of glutathione in the treatment of acetaminophen toxicity and in the therapy of nephropathic cystinosis. Low doses of cysteamine, approximately 1 to 25 mg per kg body weight, increase prolactin secretion. In contrast, high doses of cysteamine, approximately 50–400 mg per kg body weight, decrease prolactin secretion. Preferably, the salt, cysteamine HCl, is administered orally once or twice each day to achieve the desired levels of prolactin secretion. It will be understood by those skilled in the art that other sulfhydryl reducing agents could be used to increase prolactin secretion in accordance with the present invention.

Peripherally acting dopamine receptor type-2 antagonists, such as metoclopramide and domperidone, stimulate pituitary prolactin secretion with minimal effects on the central nervous system. Preferably, an intravenous or oral dose of approximately 5 to 20 mg of the antagonists is administered to a patient twice each day to enhance prolactin secretion. Dopamine antagonists are particularly useful in the treatment of critically ill patients who have received dopamine infusions because dopamine potently suppresses prolactin secretion. It will be understood by those skilled in the art that centrally acting dopamine antagonists, such as haloperidol, could be used to increase prolactin secretion in patients that are agitated, psychotic or suffering from situational ICU psychosis. Alternatively, peripherally acting dopamine type-2 agonists could be administered to lower prolactin secretion.

An intramuscular dose of approximately 0.1 to 2.0 mg of the neurophysin fragment known as the pituitary prolactin releasing factor (or glycopeptide 1–39) can also be an effective stimulant of prolactin secretion. This factor, also known as "posterior pituitary natriuretic factor", normally contains the amino acid sequence Leu-Gln-Pro-Gly-Val-Leu or a significant portion of the above-described amino acid sequence. It will be understood by those of ordinary skill in the art that any structural analog of the described amino acid sequence could also stimulate pituitary prolactin secretion.

Androgen Therapy

As discussed above, in order to maintain normal physiological prolactin levels, prolactin therapy may be used instead of, or conducted in combination with androgen therapy. Androgens are the hormones that cause most of the masculinizing changes that occur in males during puberty. However, low levels of androgens are also present in normal females. In the male, androgens are produced in the interstitial or Leydig cells found in the spaces between the seminiferous tubules of the testis. The most important androgen secreted by the testis is testosterone. The testis also secretes small amounts of another potent androgen, dihydrotestosterone, as well as androstenedione and dehydroepiandosterone, which are weak androgens. Plasma levels of testosterone in males are about 0.6 microgram per deciliter after puberty and do not appear to vary significantly with age. Testosterone is present in the plasma of women in concentrations of approximately 0.03 micrograms per deciliter and is derived in approximately equal parts from the ovaries, the adrenals, and by peripheral conversion of other hormones. In many target tissues, testosterone is converted to dihydrotestosterone by the enzyme 5-alpha reductase.

Testosterone is rapidly absorbed when administered orally. However, it is largely converted to inactive metabolites. Testosterone can be administered parenterally, but it has a more prolonged absorption time and greater activity when esterified. The testosterone derivatives, methyltestosterone and fluoxymesterone, are active when administered orally. A substantial group of synthetic steroids exhibit androgenic effects. These compounds include testosterone cypionate, testosterone enanthate, testosterone propionate, androstenedione, dehydropepiandrosterone (DHEA), methandrostenoione (metandienone), oxymetholone, ethylestrenol, oxandrolone, nandrolone phenpropionate, nandrolone decanoate, stanozolol, and dromostanolone propionate.

In accordance with the present method, an androgen such as testosterone, dihydrotestosterone, methyltestosterone or fluoxymesterone is administered orally or intramuscularly in a dosage of 2–50 mg per day, or an androgen such as testosterone cypionate, testosterone enanthate, or testosterone propionate is administered intramuscularly or in a controlled release implant of the type such as the Silastic implant (Norplant™) in a dosage of 5–20 mg per day or 10–200 mg per week until the desired effects, but with minimal side effects (such as hair growth) are achieved as determined clinically. Most preferably, androgen therapy is achieved by using one of the androgens other than dihydrotestosterone, used in the examples below, because of the occurrence of facial hair in women and prostate enlargement in men.

Estrogen Therapy

The major estrogens produced by women are estradiol (estradiol-17beta, $E_2$), estrone ($E_1$), and estriol ($E_3$). Estradiol appears to be the major secretory product of the ovary. Although some estrone is produced in the ovary, most of the estrone and estriol is formed in the liver from estradiol or in peripheral tissues from androstenedione and other androgens. In normal women, estradiol is produced at a rate that varies during the menstrual cycle. Plasma levels of estradiol vary during the menstrual cycle from a low of 50 pg/ml to as high as 350–850 pg/ml at the time of the preovulatory peak. Post-menopausal women and women who have undergone ovariohysterectomies exhibit lower levels of estrogens.

A number of chemical alterations have been produced in the natural estrogens to increase their therapeutic effectiveness when administered orally. The resulting steroids include ethinyl estradiol, mestranol and quinestrol. In addition to these steroidal estrogens, a variety of nonsteroidal compounds having estrogenic activity have been synthesized and are used clinically. These include diethylstilbestrol, chlorotrianisene and methallenestril. The average replacement doses for several commonly used estrogens is set forth below in Table 1.

TABLE 1

Average Replacement Doses for Commonly Used Estrogens

| Estrogen | Average Replacement Dose |
| --- | --- |
| ethinyl estradiol | 0.005–0.02 mg/d |
| micronized estradiol | 1–2 mg/d |
| estradiol cypionate | 2–5 mg every 3–4 weeks |
| estradiol valerate | 2–20 mg every other week |
| estropipate | 1.25–2.5 mg/d |
| conjugated, esterified, or mixed estrogenic substances: | |
| oral | 0.3–1.25 mg/d |
| injectable | 0.2–2 mg/d |
| topical | transdermal patch |
| diethylstilbestrol | 0.1–0.5 mg/d |
| quinestrol | 0.1–0.2 mg/week |
| dienestrol | ... |
| chlorotrianisene | 12–25 mg/d |
| methallenestril | 3–9 mg/d |

Oral administration of estrogens often results in adverse hepatic effects. These hepatic effects can be minimized by routes of administration that avoid first-pass hepatic exposure, such as topical (vaginal) or transdermal administration.

Therefore, in accordance with the present method, in postmenopausal women or women who have undergone ovariohysterectomies, the combined prolactin and androgen therapy is conducted in combination with estrogen therapy that restores physiologic estrogen levels to pre-menopausal or pre-hysterectomy levels. In post-menopausal women who have not undergone hysterectomy, it is most convenient to prescribe estrogen on the first 21–25 days of each month. The recommended dosages of estrogen are 0.3–1.25 mg per day of conjugated estrogen or 0.01–0.02 mg per day of ethinyl estradiol. In all cases, however, just as in current estrogen replacement therapy, the appropriate dosage must be titered for each individual, in accordance with standard procedures.

It will be understood by those skilled in the art that the desired dose, administration schedule, and optimal method of administration for maintaining or restoring physiological prolactin concentrations to normal levels can be determined by administering the prolactin (or prolactin agonist or antagonist), androgen and estrogen, if necessary, at an initial dosage, monitoring prolactin blood levels, and increasing or decreasing the dosage or method of administration to achieve the desired physiologically normal levels of prolactin in the blood.

The methods and compositions for preventing or restoring lacrimal gland atrophy will be further understood with reference to the following non-limiting examples.

EXAMPLE 1

Sexual Dimorphisms of Rabbit Lacrimal Gland Function

Male and female rabbits were sacrificed prepubertally (1 kg body weight), during mid puberty (2 kg), and at sexual maturity (3.5 kg). The lacrimal gland from each animal was surgically removed and gland fragments were transferred into ice-cold isolation buffer as quickly as possible. Fragments were minced with scissors while immersed in ice-cold buffer, then homogenized. The homogenates were subjected to a cycle of four differential sedimentation steps, and the pooled supernatant fractions were subjected to isopycnic centrifugation on sorbitol gradients as described by Yiu et al., *J. Membrane Biol.* 102:185–194 (1988) and Bradley et al., *Invest. Ophthalmol. Vis. Sci.* 31:977–986 (1990), both of which are incorporated by reference herein. Protein in subcellular fractions was determined with a BioRad assay kit (BioRad, La Jolla, Calif.)

Total protein, which reflects lacrimal gland weight, is presented in FIG. 1. The results of several measures of lacrimal gland function are presented in FIG. 2. The right-hand side of FIG. 2 shows the total activity of each parameter and the left-hand side shows the specific activity (total activity divided by protein).

Na,K-ATPase was determined with the $K^+$-dependent p-nitrophenylphosphatase ($K^+$-PNPPase) reaction described by Murer et al., *Biochem. Biophys. Acta.* 433:509–519 (1976), which is incorporated by reference herein. $K^+$-PNPPase activity closely parallels the $Na^+$, $K^+$-ATPase activity measured as ouabain-sensitive hydrolysis of ATP in the presence of $Na^+$ and $K^+$. Neurotransmitter receptor ligand binding was measured essentially by the method described by Bradley et al., *Invest. Ophthalmol. Vis. Sci.* 31:977–986 (1990), which is incorporated by reference herein.

The results indicate several gender-related differences in the lacrimal gland of sexually mature rabbits relating to ion transport and stimulus-secretion coupling. For example, in accordance with their smaller net weight, lacrimal glands from females contained approximately 30% less total protein and significantly fewer beta-adrenergic receptors. However, female lacrimal glands appeared to contain more Na,K-ATPase pumps and a two-fold greater Na,K-ATPase specific activity.

EXAMPLE 2

Effect of Hypophysectomy on Female Rat Lacrimal Gland Function

Hypophysectomized female rats were compared with pituitary-intact females and with hypophysectomized females treated with various hormones. One day after surgical removal of the pituitary gland, adult female rats were treated with steroid hormones, prolactin, or bromocriptine. The treatment was as follows. Steroid hormones were dissolved in corn oil and injected subcutaneously, once per day. Prolactin was dissolved in normal saline and injected subcutaneously, twice per day. Bromocriptine was dissolved in 100% ethanol, then diluted 1:1 with saline and injected into animals twice per day.

One group was treated twice daily with 5 mg/kg prolactin for two days. A second group was given the estrogen diethylstilbestrol (DES, 50 microgram/rat) daily for two days. A third group was given 1 mg/rat dihydrotestosterone (DHT) daily for two days. A sham operated group served as control. All rats were sacrificed on the morning of the third day after treatment was begun. There were five rats in each group.

Total protein content, Na,K-ATPase activity, and cholinergic and beta-adrenergic binding activities were determined as described in Example 1 above.

Figure 3A:
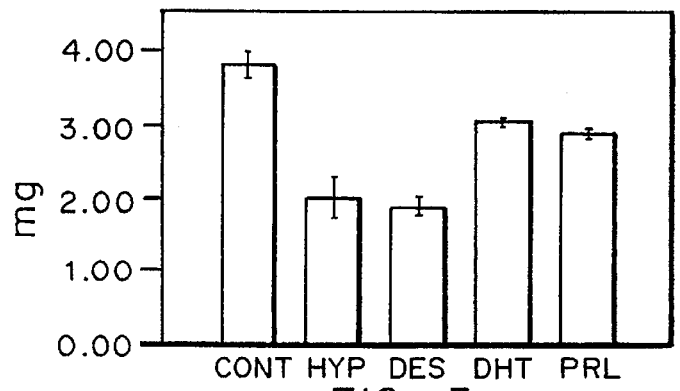
FIGS. 3a–h are bar graphs showing the effect of hypophysectomy and hormone treatment on female rat lacrimal gland functions. "Cont" is an abbreviation for control. "HYP" is an abbreviation for hypophysectomized. "DES" is an abbreviation for diethylstilbestrol. "PRL" is an abbreviation for prolactin. "DHT" is an abbreviation for dihydrotestosterone.
Figure 3B:
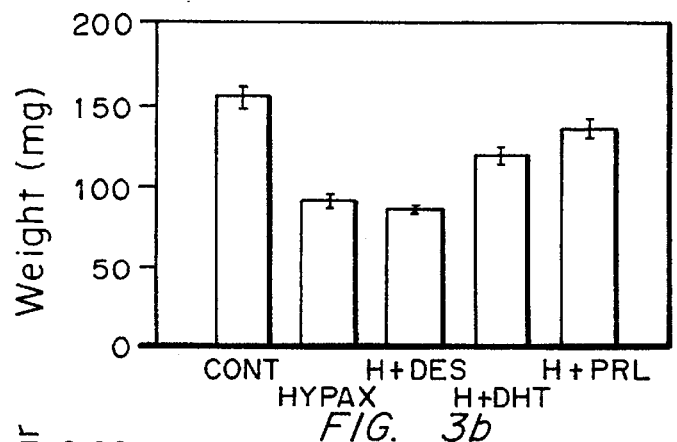
Figure 3C:
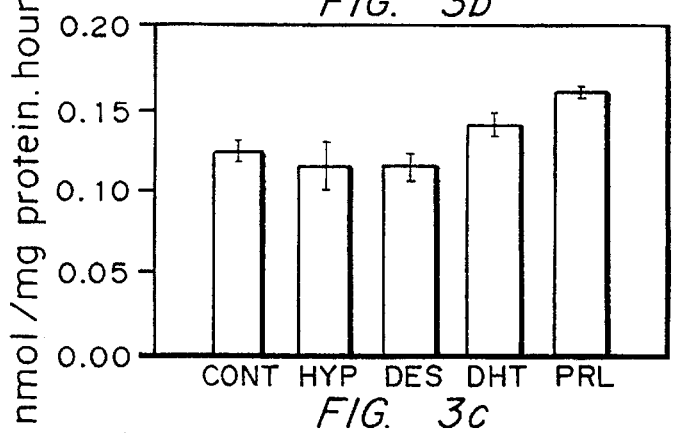
Figure 3D:
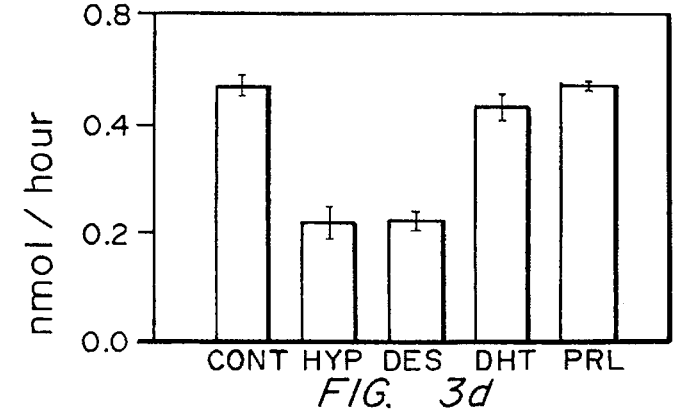
Figure 3E:
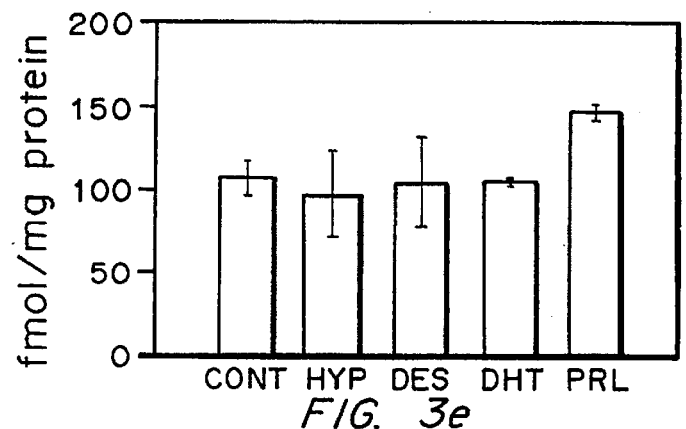
Figure 3F:
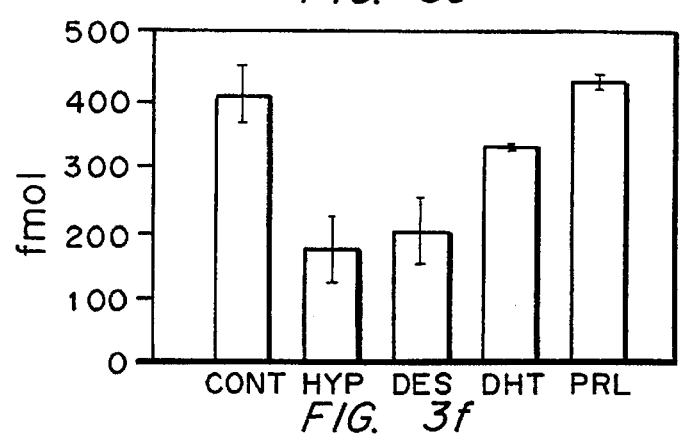
Figure 3G:
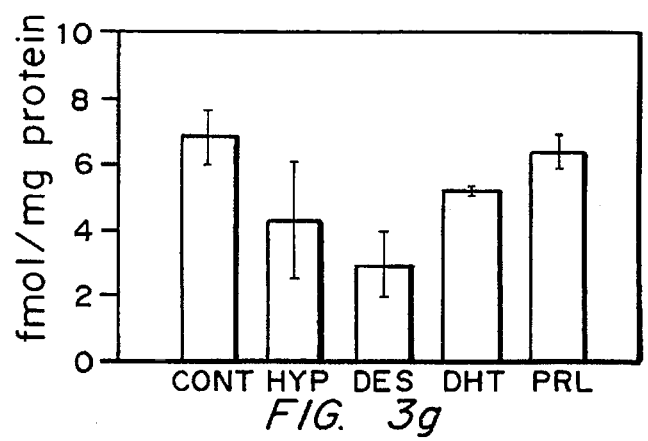
Figure 3H:
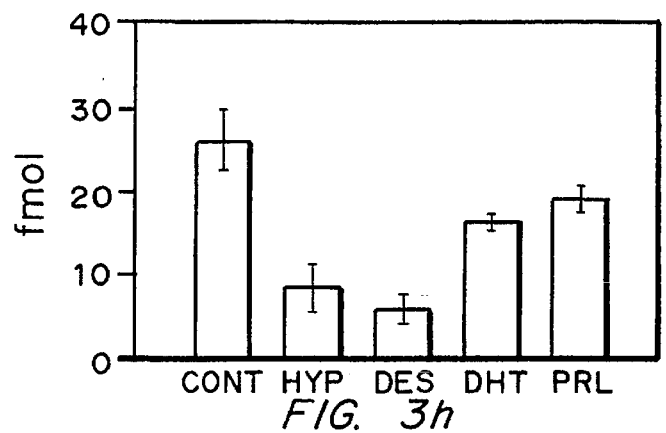
Figure 4A:
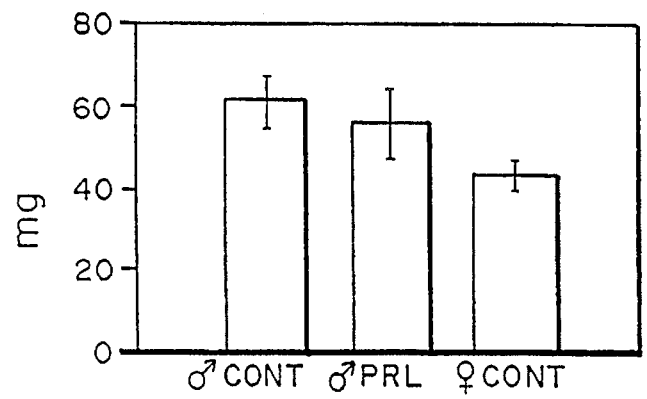
FIGS. 4a–d are bar graphs showing lacrimal gland functional markers in control female and prolactin-treated male rabbits.
Figure 4B:
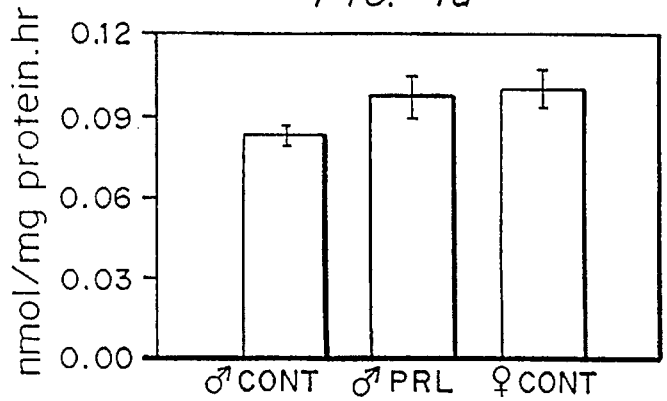
Figure 4C:
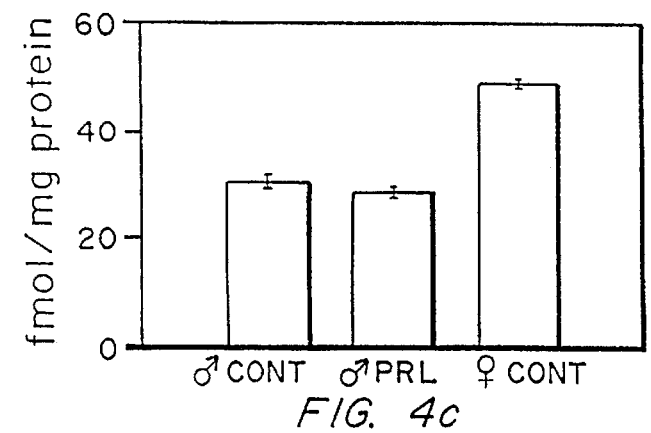
Figure 4D:
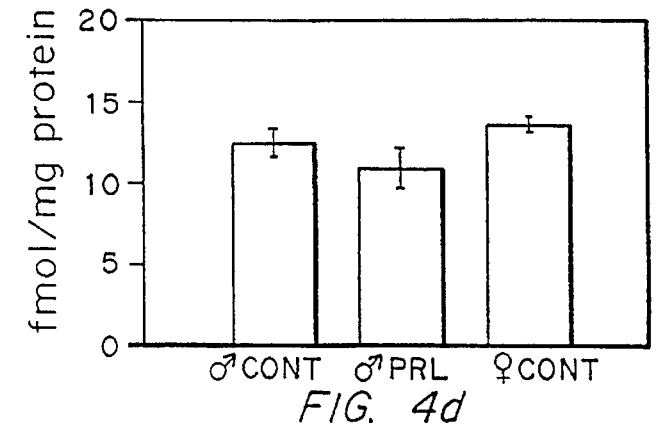

FIGS. 3a and 3b show the effects of the treatments on the total protein content and weight of the lacrimal glands. FIGS. 3c–h present the Na,K-ATPase activity, cholinergic and beta-adrenergic binding activities in these lacrimal glands. Total activity is on the right and the specific activity on the left. The significance of these results is discussed below.

Hypophysectomy deprives the gonads and adrenal glands of trophic stimulation, thus reducing the levels of estrogens, progesterone and androgens from the ovaries, and of androgens and glucocorticoids from the adrenals. Hypophysectomy caused significant decreases in lacrimal gland weight, total Na,K-ATPase, muscarinic cholinergic ligand binding, and beta-adrenergic ligand binding. The decreases in Na,K-ATPase and muscarinic receptor activities were approximately coordinate with the decrease in protein, so that their specific activities remained approximately constant. In contrast, beta-adrenergic receptor activity appeared to decrease even more than total protein, although the apparent change in specific activity was not statistically significant.

Dihydrotestosterone (DHT) significantly increased muscarinic cholinergic ligand binding and beta-adrenergic ligand binding in hypophysectomized animals, although the total activities remained significantly less than in pituitary-intact animals. DHT also reversed about half the hypophysectomy-induced decrease in total protein, and it reversed virtually the entire decrease in total N,K-ATPase activity, thus increasing the Na,K-ATPase specific activity above the value in pituitary-intact animals. In contrast, DES, a potent estrogen, failed to increase muscarinic receptor activity; it appeared to further decrease the beta-adrenergic receptor activity, although this effect was not statistically significant.

These results indicate that androgens exert positive effects on several parameters related to the functional status of the female lacrimal gland, they exert these effects independently of pituitary peptides, and at the doses administered (doses which maintain male characteristics), androgens do not completely reverse the hypophysectomy-induced changes.

Prolactin reversed 50% of the hypophysectomy-induced decreases in lacrimal gland weight, total protein, and beta-adrenergic ligand binding, so that the receptor specific binding activity remained at the level of pituitary-intact and hypophysectomized females. Prolactin also partially restored the Na,K-ATPase and muscarinic ligand binding activities, thereby increasing their specific activities above the levels in pituitary-intact females. Thus, the higher circulating prolactin levels in the female tend to suppress lacrimal production of prolactin while the lower circulating prolactin levels in the male are insufficient to provide the lacrimal gland with adequate levels of prolactin. Thus, the lacrimal gland in the male must produce its own prolactin.

EXAMPLE 3

Effects of Prolactin Treatment on Functional Parameters of the Lacrimal Gland in Intact Male Rabbits.

In this experiment, three control and three prolactin-treated adult male rabbits were examined in accordance with the procedures described above in Examples 1 and 2 except that the prolactin dose was 2.8 mg/kg in the morning and 1.9 mg/kg in the afternoon of day 1. This was considerably less prolactin, both in mg/kg and in duration (two injections on one day instead of four injections over two days) than in the experiment with hypophysectomized female rats (Example 2). The animals were sacrificed on the morning of day two. Results are presented in FIG. 4.

The results demonstrate that even this brief prolactin treatment increased the specific activity of Na,K-ATPase in the lacrimal glands of male rabbits.

EXAMPLE 4

Reversal of Lacrimal Gland Regression in Hypophysectomized Female Rats by Combined Dihydrotestosterone and Prolactin Treatment Adult female rats (four per group) were hypophysectomized on day 0, then treated either with 10 mg/kg prolactin (PRL), 1 mg dihydrotestosterone (DHT), or both on days 1 and 2 as described above in Example 1 and killed on day 3. Na,K-ATPase, beta adrenergic and muscarinic cholinergic receptor binding and protein were measured in total lacrimal gland membrane samples as described above in Example 1.

As shown in FIG. 5, hypophysectomy decreased gland mass and decreased total membrane protein content by 50%. Receptor and Na,K-ATPase contents were decreased in parallel with protein, i.e., with no changes of specific activity. Dihydrotestosterone and prolactin each partially reversed the loss of gland mass and protein and increased the Na,K-ATPase specific activity to greater than control values. In addition, dihydrotestosterone (partially) and prolactin (totally) reversed the decreases in total receptor binding activities. Thus, dihydrotestosterone and prolactin appear to exert general, trophic actions on the lacrimal gland and specific actions on lacrimal Na,K-ATPase and neurotransmitter receptors.

Modifications and variations of the present compositions and methods for treating exocrine gland atrophy will be obvious to those skilled in the art from the foregoing detailed description. Such modifications and variations are intended to come within the scope of the appended claims.

We claim:

1. A method of preventing or reversing secretory exocrine gland atrophy in a mammal comprising administering to the mammal in need thereof a synergistic amount effective to prevent or reverse secretory exocrine gland atrophy of the combination of a compound modulating endogenous prolactin levels and an androgen selected from the group consisting of testosterone and dihydrotestosterone, wherein the secretory exocrine gland is selected from the group consisting of salivary glands, lacrimal glands, mucus-secreting glands, glands of the gastrointestinal system, glands of the urinary system, and vaginal glands.

2. The method of claim 1 wherein the combination of the prolactin modulating compound and the androgen is effective to increase lacrimal gland function.

3. The method of claim 1 wherein the prolactin modulating compound is selected from the group consisting of isolated prolactin and recombinant prolactin.

4. The method of claim 1 wherein the prolactin modulating compound is a compound capable of modulating endogenous pituitary prolactin secretion.

5. The method of claim 4 wherein the compound modulating prolactin secretion is selected from the group consisting of prolactin secretion stimulants and inhibitors.

6. The method of claim 1 wherein the combination of the prolactin modulating compound and the androgen is administered subcutaneously.

7. The method of claim 6 wherein the combination of the prolactin modulating compound and the androgen is administered via a controlled release implant.

8. The method of claim 1 wherein the combination of the prolactin modulating compound and the androgen is administered orally.

9. The method of claim 1 wherein the combination of the prolactin modulating compound and the androgen is administered intramuscularly.

10. A composition for the treatment of secretory exocrine gland atrophy comprising synergistic effective amounts of an androgen selected from the group consisting of testosterone and dihydrotestosterone and a compound modulating endogenous prolactin levels to prevent or reverse atrophy or maintain function of a secretory exocrine gland, wherein the secretory exocrine gland is selected from the group consisting of salivary glands, lacrimal glands, mucus-secreting glands, glands of the gastrointestinal system, glands of the urinary system, and vaginal glands, in a physiologically acceptable carrier.

11. The composition of claim 10 wherein the prolactin modulating compound is selected from the group consisting of isolated prolactin and recombinant prolactin.

12. The composition of claim 10 wherein the androgen is testosterone which is made synthetically.

13. The composition of claim 10 further comprising estrogen or an estrogen analog in an amount effective to increase lubrication of an estrogen target tissue.

14. A composition for the treatment of secretory exocrine gland atrophy comprising an effective amount of the combination of an androgen and a compound modulating endogenous prolactin levels, in a physiologically acceptable carrier, to prevent or reverse atrophy or maintain function of a secretory exocrine gland, wherein the exocrine gland is the lacrimal gland.

15. The composition of claim 10 wherein the prolactin modulating compound is a compound capable of modulating endogenous pituitary prolactin secretion.

16. The composition of claim 15 wherein the compound modulating prolactin secretion is selected from the group consisting of prolactin secretion stimulants and inhibitors.

17. The composition of claim 10 in a controlled release implant.

18. The method of claim 1, wherein the compound modulating endogenous prolactin levels is bromocriptine and the androgen is testosterone.

19. The composition of claim 10, wherein the androgen is testosterone and the compound modulating endogenous prolactin levels is bromocriptine.

* * * * *